United States Patent [19]
Takehara et al.

[11] Patent Number: 6,077,971
[45] Date of Patent: Jun. 20, 2000

[54] METHOD FOR PURIFYING HOMOCYSTINE

[75] Inventors: Jun Takehara; Shuji Ichikawa; Hiroshi Iwane, all of Ibaraki; Hirotaka Ryutou, Fukuoka; Kenichi Sugimoto, Fukuoka; Toshihiko Yahata, Fukuoka, all of Japan

[73] Assignee: Mitsubishi Chemical Corporation, Tokyo, Japan

[21] Appl. No.: 09/204,239

[22] Filed: Dec. 3, 1998

[30] Foreign Application Priority Data

Dec. 5, 1997 [JP] Japan ................................ 9-335549

[51] Int. Cl.⁷ ...................... C07C 227/40; C07C 227/14
[52] U.S. Cl. ........................ 562/554; 562/556; 562/557
[58] Field of Search ................... 562/554, 556, 562/565

[56] References Cited

U.S. PATENT DOCUMENTS 4,550,199  10/1985  Karrenbauer et al. .

FOREIGN PATENT DOCUMENTS 0 120 182  10/1984  European Pat. Off. .
0 844 239  5/1998  European Pat. Off. .
12 19 903  1/1971  United Kingdom .

OTHER PUBLICATIONS

Miyazaki, H. Preparations of Optically Active Homocysteine and Homocystine by Asymmetric Transformation or (RS)–1,3–Thiazane–4–carboxylic Acid Bull. Chem. Soc. Jpn. vol. 66 No. 2 pp 536–540, 1993.

Lipton, S.H. "Peroxide Oxidation Products of Homocystine and Lanthionine" J. Agric. Food Chem. vol. 26 No. 6 pp 1406–1409, 1976.

Butz, L. W. et al "The Formation of a Homologue of Cystine by the Decomposition of Methionine with Sulfuric Acid" J. Biol. Chem. vol. 99 pp 135–142, 1993.

*Primary Examiner*—Gary Geist
*Assistant Examiner*—Leigh C. Maier
*Attorney, Agent, or Firm*—Oblon, Spivak, McClelland, Maier & Neustadt, P.C.

[57] ABSTRACT

Disclosed is a method for purifying homocystine comprising treating crude homocystine with a base, a method for purifying homocystine comprising recovering homocystine by neutralizing an alkaline aqueous solution of crude homocystine with an acid, and a homocystine powder containing 1,000 ppm or less of a polysulfide.

17 Claims, No Drawings

METHOD FOR PURIFYING HOMOCYSTINE

FIELD OF THE INVENTION

The present invention relates to a method for purifying homocystine and a high purity homocystine powder. Homocystine or homocysteine thiolactone obtained by reduction and cyclization thereof is a useful substance as an intermediate for synthesizing various organic compounds including medicines and agricultural chemicals.

BACKGROUND OF THE INVENTION

As methods for producing DL-homocystine, methods using inexpensive and easily available DL-methionine as a raw material are known. For example, *J. Biol. Chem.*, 99, 135 (1932–33) describes a method of producing DL-homocystine by heating DL-methionine in a large excess of sulfuric acid. Further, a method of producing DL-homocystine comprising reducing DL-methionine with metallic sodium in liquid ammonia to DL-homocysteine, followed by oxidization thereof is also known (West German Patents 3,309,761 and 2,547,672).

The present inventors have proposed a method of reacting methionine with sulfuric acid in the coexistence of a hydrogen halide (JP-A-10-204055 (the term "JP-A" as used herein means an "unexamined published Japanese patent application"): details thereof will be described below).

However, homocystine produced by these methods contains by-products such as polysulfides in small amounts, particularly, L-homocystine further contains by-products such as mesohomocystine in small amounts in addition. Accordingly, it cannot be used as it is as an intermediate for synthesizing various organic compounds including medicines and agricultural chemicals. For obtaining a high purity product, a further purifying process of crystallization is required. However, repetition of simple crystallization cannot provide the high purity product, and up to the present time, an industrial purifying method for obtaining the high purity product has not been established.

SUMMARY OF THE INVENTION

An object of the present invention is to provide an industrially advantageous method for purifying crude homocystine containing impurities such as polysulfides and mesohomocystine to obtain particularly high purity D- or L-homocystine.

Another object of the present invention is to provide a DL-, D- or L-homocystine powder having a large crystal size and advantageous in industrial handling such as filtration properties.

That is to say, the present invention provides (1) a method for purifying homocystine comprising treating crude homocystine with a base; (2) a method for purifying homocystine comprising recovering homocystine by adding an acid such as an organic acid to an alkaline aqueous solution of homocystine obtained by treating crude homocystine with a base; (3) a homocystine powder containing 1,000 ppm or less of a polysulfide; and (4) the above-mentioned homocystine powder, wherein the content of mesohomocystine is 1% by weight or less.

DETAILED DESCRIPTION OF THE INVENTION

The present invention will be described in detail below.

Method for Producing Crude Homocystine

There is no particular limitation on crude homocystine to be purified in the present invention. However, the purification of homocystine produced from methionine as a starting material is particularly effective, because such homocystine contains impurities such as polysulfides which cannot be removed by other methods.

Processes for producing such crude homocystine from methionine as a starting material include the following processes:

(1) A process of producing DL-homocystine comprising reducing DL-methionine with metallic sodium in liquid ammonia to DL-homocysteine, followed by oxidation thereof (West German Patents 3,309,761 and 2,547,672); and (2) A process of producing DL-, D- or L-homocystine comprising heating DL-, D- or L-methionine at a temperature of 60 to 150° C. in the presence of sulfuric acid and a hydrogen halide (JP-A-10-204055).

For the industrial production, the process of (2) is more preferred.

As both the racemi modification and the optically active substance of methionine used as the raw material in the above-mentioned reaction, ones obtained through any course can be used. The racemi modification is industrially produced by, for example, adding methanethiol to acrolein as a raw material, and thereafter conducting the Strecker reaction, followed by hydrolysis.

Of the above-mentioned reactions, the reaction of (2) described above, the industrially preferred method, is conducted by heating DL-, D- or L-methionine together with sulfuric acid and a hydrogen halide. In this case, a solvent may be used or not be used. As sulfuric acid, pure sulfuric acid or concentrated sulfuric acid having a concentration of 10% by weight or more is used, and sulfuric acid is used in an amount of at least 0.5 time based on the mole of methionine, and preferably in an amount of 1 to 10 times based on the mole of methionine.

As the hydrogen halides, hydrogen chloride, hydrogen bromide and hydrogen iodide are used, and hydrogen bromide is preferred. These hydrogen halides may be used either in the gas form, or as hydrohalogenic acids having a concentration of 20% by weight or more obtained by allowing them to be absorbed by water. They are used in an amount at least equimolar with methionine.

The heating temperature ranges from 60 to 150° C., and preferably from 80 to 140° C. For the reaction time, the reaction is usually completed in 1 to 30 hours, although it varies according to the heating temperature and the amounts of sulfuric acid and hydrogen halides used. The reaction is preferably conducted with stirring in a stream of an inert gas such as nitrogen for removing sulfur dioxide and methyl halides produced. After the reaction is completed, homocystine produced is dissolved in a reaction solution as the sulfate. Accordingly, it is neutralized with a base such as an aqueous solution of sodium hydroxide, and crystals precipitated are separated by filtration and washed with water. Thus, homocystine can be easily obtained.

When indicated by a reaction scheme, this process is considered to be as follows:

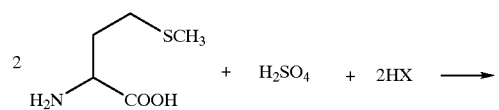

-continued

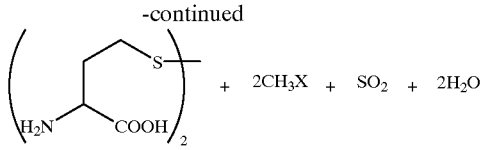

wherein X represents a halogen atom.

According to this process, crude homocystine can be obtained in high yield by use of a hydrogen halide. As shown in the following scheme, it is considered that the hydrogen halide reacts with the dimethylsulfonium salt produced by the reaction of methionine with sulfuric acid to convert it to methionine.

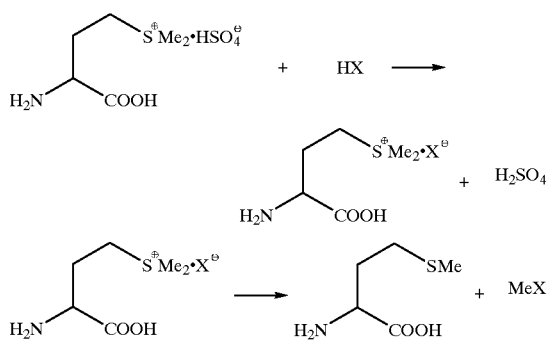

wherein Me represents a methyl group; and X represents a halogen atom.

Purification of Crude Homocystine

Crude homocystine obtained by the filtration and washing of the above-mentioned precipitated crystals contains impurities such as polysulfides in small amounts. Further, when L-methionine is used as a raw material in the above-mentioned process, crude homocystine contains by-products such as mesohomocystine as impurities in small amounts, in addition to polysulfides. This is therefore treated with an aqueous solution of a base in an excess amount to crude homocystine (successive purifying method). It is also possible to perform the purifying procedure of the present invention at the same time by use of an excess amount of a base more than the amount necessary for neutralization in neutralizing an aqueous solution containing homocystine sulfate obtained in the above-mentioned production of crude homocystine (direct purifying method).

As the base, an aqueous solution of an alkaline metal hydroxide, ammonia or an amine can be used. An aqueous solution of an alkaline metal hydroxide is preferred, and an aqueous solution of sodium hydroxide is more preferred.

The base is sufficiently used in an amount at least equimolar with crude homocystine, preferably in an amount of twice or more based on the mole of crude homocystine, and more preferably in an amount of 3 to 10 times based on the mole of crude homocystine. When the base treatment is conducted together with the neutralization of the aqueous solution of homocystine sulfate produced in the course of producing crude homocystine by the direct purifying method, the above-mentioned amount of the base is required, in addition to the amount of the base necessary for the neutralization. The reaction temperature ranges from 0 to 60° C., and preferably from 0 to 30° C. For the reaction time, the decomposition of the impurities, such as polysulfides, is substantially completed in 0.5 to 5 hours, although it varies according to the reaction temperature and the amount of the base used.

When the aqueous solution of homocystine sulfate is neutralized with the base to precipitate crude L-homocystine in the successive purifying method, it is also possible to obtain a crude L-homocystine powder low in the meso-homocystine content, utilizing that the precipitating rate of mesohomocystine produced as a by-product is slower than that of L-homocystine. That is to say, crude L-homocystine reduced in the mesohomocystine content can be obtained by neutralizing the above-mentioned aqueous solution of homocystine sulfate, preferably using an alkaline metal hydroxide as the base, so as to provide pH 5 to 8 within 4 hours, preferably within 3 hours, and particularly within 2 hours.

Further, homocystine is dissolved as a salt in the aqueous solution in which crude homocystine is dissolved again by use of the base in the above-mentioned successive purifying procedure, or in the treated solution in which the sulfate is treated with an excess amount of the base in the above-mentioned direct procedure. Accordingly, high purity homocystine can be easily obtained by neutralizing the solution with acid selected one or more from the group consisting of an mineral acid such as hydrochloric acid or sulfuric acid, and an organic acid such as formic acid, acetic acid or oxalic acid, separating precipitated crystals by filtration, and washing them with water. Decomposed products of the impurities are water-soluble, so that they can be easily removed at the time of the filtration. In particular, when the above-mentioned organic acid is added to the solution obtained by treating the aqueous solution containing homocystine sulfate obtained in the above-mentioned production of homocystine with an excess amount of the base, or the solution containing the salt of homocystine or L-homocystine obtained by dissolving isolated crude homocystine again in the aqueous solution of the alkaline metal hydroxide, homocystine or L-homocystine precipitated is preferably increased in crystal size.

Homocystine obtained by the above-mentioned purifying methods contains 1000 ppm or less of polysulfides which are impurities, and particularly, in the case of L-homocystine, the content of mesohomocystine which is an impurity is 1% by weight or less.

EXAMPLE

The present invention will be further illustrated in greater detail with reference to the following examples, which are, however, not to be construed as limiting the invention, as long as they do not depart from the scope thereof.

Liquid chromatography was used for analysis of reaction solutions, cakes separated by filtration and alkaline solutions, quantitative analysis was carried out by the absolute calibration method, the conversion rate, the selection rate and the remaining rate of L-homocystine (LHSS) were determined according to the following equations, and the optical purity was determined with a UV detector. Using liquid chromatography, the area percent of L-homocystine was determined on the basis of each peak area of L-homocystine, mesohomocystine and polysulfides, and using a preparation of L-homocystine, the purity (absolute calibration) of L-homocystine was measured.

Conversion rate (%)=100×(the mole number of a reacted raw material)/(the mole number of a charged raw material)

Selection rate (%)=100×(the mole number of a desired product (note 1)×2)/(the mole number of the desired product (note 1)×2+the mole number of by-products (note 2))

Note 1: homocystine sulfate
Note 2: methionine-S-methylphosphonium sulfate and homocysteine sulfate LHSS remaining rate (%)100×(the concentration of LHSS in an alkaline solution after test time)/(the concentration of LHSS in the alkaline solution before test time)

Example 1

Production of Crude Homocystine

In a glass reaction flask having a content volume of 1000 ml, 300 g (2.01 moles) of L-methionine and 346.4 g (2.01 moles) of a 47% aqueous solution of HBr were placed together with a stirrer, and 414.7 g (4.02 moles) of 95% sulfuric acid was added thereto under ice cooling, followed by heating at 100° C. for 9 hours with stirring in a stream of nitrogen.

The analysis of the reaction solution by liquid chromatography showed that 8.2 g (0.04 mole) of L-methionine sulfate, 156.4 g (0.43 mole) of L-homocystine sulfate and 257.3 g (0.83 mole) of L-methionine-S-methylsulfonium sulfate were produced. The conversion rate was 98%, and the selection rate was 50%.

Then, the reaction solution was adjusted to pH 7 with a 10% aqueous solution of sodium hydroxide while cooling the reaction solution, and a precipitate developed was separated by filtration, washed with water and dried to obtain 110.4 g of crude L-homocystine (polysulfide content: 1.1% by weight).

The yield based on L-methionine was 41%, and the optical purity was 99.7% or more. Further, the purities measured by use of a liquid chromatograph (LC) were 85.4% (area %) and 96% (absolute calibration).

Purification of Crude Homocystine

Then, 110.4 g of crude L-homocystine thus obtained was dissolved in 750 ml (1.5 moles) of a 2 N aqueous solution of sodium hydroxide, followed by stirring at room temperature for 3 hours. Subsequently, the solution was neutralized with 35% hydrochloric acid at a temperature of 30° C. or less, and a precipitate developed was separated by filtration, washed with water and dried to obtain 107.7 g of L-homocystine (polysulfide content: 0.08% by weight).

The yield based on L-methionine was 40%, the optical purity was 99.9% or more, and the purities measured by use of an LC were 99% or more (area %) and 100% (absolute calibration).

Comparative Example

Recrystallization Using Acid

Crude homocystine (109.5 g, the purities measured by use of an LC were 87% (area %) and 96% (absolute calibration)) obtained in a manner similar to that of Example 1 was dissolved in 35% hydrochloric acid at room temperature. Then, the resulting solution was neutralized with a 1 N aqueous solution of sodium hydroxide at a temperature of 30° C. or less, and a precipitate developed was separated by filtration, washed with water and dried to obtain 105 g of L-homocystine. The yield based on L-methionine was 39%, and the optical purity was 99.9% or more. Accordingly, the mesohomocystine content was 0.1% or less, but the purities measured by use of an LC were 87% (area %) and 98% (absolute calibration). Further, the polysulfide content was 1.0% by weight, and results thereof were far inferior to those of recrystallization using the base (Example 1 described above).

Example 2

Production of Crude Homocystine

In a glass reaction flask having a content volume of 1000 ml equipped with a stirring blade and a cooling pipe, 150 g (1.01 moles) of L-methionine was mixed with 346.4 g (2.01 moles) of a 47% aqueous solution of HBr and dissolved therein at room temperature. After 201.0 g (2.01 moles) of 95% sulfuric acid was added thereto in a stream of nitrogen, the flask was immersed in an oil bath heated at 145° C., and the solution was refluxed with stirring at an interior temperature of 125° C. for 5 hours with stirring. (Reaction solution 1)

The analysis of the above-mentioned reaction solution 1 by liquid chromatography showed that 2.6 g (0.01 mole) of L-methionine sulfate, 112.5 g (0.31 mole) of L-homocystine sulfate, 12.4 g (0.03 mole) of mesohomocystine sulfate and 52.7 g (0.17 mole) of L-methionine-S-methylsulfonium sulfate were produced. The conversion rate was 99%, and the selection rate was 61%.

Then, the above-mentioned reaction solution 1 was transferred to a 2000-ml glass vessel, and 1160 g (4.35 moles) of a 15% aqueous solution of sodium hydroxide was added thereto for 3 hours with stirring in a constant-temperature water bath kept at 40° C. at such a rate that the interior temperature did not exceed 65° C., thereby adjusting the pH to 5.0. After a precipitate developed was filtered with suction through a 5C filter paper, it was washed with 150 g of desalted water and dried under reduced pressure at 60° C. The weight of crude L-homocystine obtained was 87.7 g (polysulfide content: 6.9% by weight). The yield based on L-methionine was 51%, and the optical purity was 93.3% (mesohomocystine: 6.7%). The purities measured by use of an LC were 69% (area %) and 78% (absolute calibration).

Reference Example 1

Production of Crude Homocystine: Comparison of Stability of L-Homocystine in Neutralizing Conditions In a 250-ml separable flask equipped with a stirrer, a thermometer and a jacket, 50 ml (76.5 g) of reaction solution 1 obtained in the production of crude homocystine of Example 2 was placed, and the interior temperature was elevated to 50° C. Then, the solution was neutralized to pH 3.5 with a 15% aqueous solution of sodium hydroxide for 10 minutes while keeping the interior temperature at 50° C. After the neutralization, 50 ml portions of the slurry were sampled with time, and quickly filtered with suction through a 5C filter paper, followed by washing with 50 ml of desalted water and drying under reduced pressure at 60° C. L-homocystine thus obtained was analyzed by liquid chromatography to determine the optical density of L-homocystine. The optical density of L-homocystine showed 91.3% after 0.5 hour, 91.2% after 5 hours, 90.7% after 10 hours and 90.7% after 24 hours. Impurities developed in the reaction, polysulfides, were water-insoluble, so that they could not be removed by filtration and the total amount of them was entrapped in crude homocystine. The content thereof showed 6.9%. (Experimental No. 3-1)

Experimental Nos. 3-2 to 3-8 were carried out in the same manner as with Experimental No. 3-1 with the exception that the neutralization temperature, the neutralization time and the pH of neutralization were each varied as shown in Table 1. After the neutralization, the optical purity of L-homocystine in filtered cakes was determined. Results are shown in Table 1.

98.1%, and the mean particle size determined with an LMS-24 manufactured by Seishin Co. was 3.4 μm. (Experimental No. 5-1)

Experimental Nos. 5-2 to 5-6 were carried out in the same manner as with Experimental No. 5-1 with the exception that the acids for precipitation shown in Table 2 were used in place of 35% hydrochloric acid. Carbonic acid gas used as the acid for precipitation is considered to react with water and relate to the reaction as carbonic acid in the reaction system in which the neutralization reaction is conducted. Results thereof are shown in Table 2.

TABLE 1

| Example 3 Experimental No. | Neutralization Temperature (° C.) | pH | Neutralization Time (minute) | Optical Density in Reaction Solution (%) | Optical Density in Filtered Cake after Neutralization | | | |
|---|---|---|---|---|---|---|---|---|
| | | | | | 0.5 hour | 5 hours | 10 hours | 24 hours |
| 3-1 | 50 | 3.5 | 10 | 90 | 91.3 | 91.2 | 91.3 | 90.7 |
| 3-2 | 50 | 5.7 | 10 | 90 | 93.7 | 92 | 91.5 | 91.4 |
| 3-3 | 50 | 7.5 | 10 | 90 | 95.7 | 95.7 | 93.8 | 93.1 |
| 3-4 | 20 | 6 | 10 | 90 | 96 | 95.5 | 94.1 | 92.9 |
| 3-5 | 60 | 7.5 | 10 | 90 | 97.1 | 97 | 96.5 | 93 |
| 3-6 | 50 | 7.5 | 120 | 90 | 96.5 | 96 | 95 | 92.1 |
| 3-7 | 50 | 7.5 | 240 | 90 | 92.1 | 92 | 91.2 | 91 |
| 3-8 | 50 | 7.5 | 480 | 90 | 91.5 | 91.3 | 91.2 | 91.1 |

Example 3

Purification of Crude Homocystine

In a 100-ml glass separable flask equipped with a stirrer, a thermometer, a pH meter and a jacket, 79.6 g (73.5 mmoles) of a 15% aqueous solution of sodium hydroxide was placed, and the temperature was lowered to 10° C. Then, 10.0 g (27.99 mmoles as L-homocystine) of crude homocystine (optical purity: 93.3%, polysulfide content: 6.7% by weight) obtained in Example 2 was added thereto and dissolved therein. After stirring at 10° C. for 3 hours, the solution was neutralized with a 35% aqueous solution of hydrochloric acid to pH 7.5, and a cake formed was filtered with suction through a No. 5C filter paper. Then, the cake was washed with 150 ml of desalted water, and dried under reduced pressure at 60° C. to obtain L-homocystine having an optical purity of 97.77% in which no polysulfide was detected in a high recovery of 98% based on charged L-homocystine.

Example 4

Purification of Crude Homocystine: Comparison for Kind of Acid for Precipitation and Particle Size of Homocystine Powder Crude homocystine (26.8 g) obtained in the production of crude homocystine of Example 2 was dissolved in 135 ml of a 15% aqueous solution of sodium hydroxide, and stirred at room temperature for 3 hours. Then, 35% hydrochloric acid was added at such a rate that the temperature did not exceed 30° C. to neutralize the solution to pH 7.5. A precipitate was washed with water and dried under reduced pressure to obtain L-homocystine. The optical purity thereof was

TABLE 2

| Example 5 Experimental No. | Acid for Precipitation | Optical Density (%) | Mean Crystal Size (μm) |
|---|---|---|---|
| 5-1 | Hydrochloric acid | 98.1 | 3.4 |
| 5-2 | Acetic acid | 98 | 17.2 |
| 5-3 | Formic acid | 98.2 | 10.3 |
| 5-4 | Oxalic acid | 98.1 | 27.4 |
| 5-5 | Sulfuric acid | 98.1 | 2 |
| 5-6 | Carbonic acid gas | 98.2 | 4.3 |

Reference Example 2

Comparison of Stability of L-Homocystine under Basic Conditions

In a 100-ml glass separable flask equipped with a stirrer, a thermometer and a jacket, 30.0 g (112.5 mmoles) of a 15% aqueous solution of sodium hydroxide was placed, and the temperature was lowered to 5° C. Then, L-homocystine having an optical purity of 100% and a purity of 100% was added at a sodium hydroxide/L-homocystine (NaOH/LHSS) molar ratio shown in Table 3 and dissolved therein. The solution was maintained at a temperature shown in Table 3 with stirring, and sampled with time at a time shown in Table 3. Then, the concentration of L-homocystine was measured according to analysis by liquid chromatography to determine the stability of L-homocystine under alkaline conditions.

TABLE 3

| Example 6 Experimental No. | Temperature (° C.) | NaOH/LHSS Molar Ratio | LHSS Remaining Rate (%) | | | | |
|---|---|---|---|---|---|---|---|
| | | | 0 hour | 30 hours | 60 hours | 120 hours | 240 hours |
| 6-1 | 5 | 3 | 100 | 99.8 | 99.5 | 99.1 | 98.3 |
| 6-2 | 5 | 4.5 | 100 | 99.6 | 99.1 | 98.3 | 96.8 |
| 6-3 | 5 | 8 | 100 | 98.3 | 96.7 | 93.7 | 87.6 |
| 6-4 | 25 | 3 | 100 | 98.2 | 96.4 | 93 | 86.7 |
| 6-5 | 25 | 4.5 | 100 | 96.8 | 93.5 | 87.5 | 76.5 |
| 6-6 | 25 | 8 | 100 | 87.1 | 76 | 57.5 | 34.5 |
| 6-7 | 55 | 4.5 | 100 | 39.9 | 16.1 | — | — |

According to the method of the present invention, high purity homocystine useful as an intermediate for synthesizing medicines and agricultural chemicals can be obtained in high yields, using methionine which is industrially easily available as a raw material. Further, the present invention can provide homocystine high in purity and large in crystal size (mean crystal diameter). Furthermore, homocystine can be stored in an alkaline aqueous solution, inhibiting the decomposition of homocystine.

What is claimed is:

1. A method for purifying homocystine comprising treating crude homocystine containing a polysulfide with a base selected from an aqueous solution of an alkaline metal hydroxide, ammonia, or amine.

2. The method according to claim 1, wherein said crude homocystine is an aqueous solution of homocystine sulfate obtained in producing homocystine, and said base is used in an excess amount to homocystine sulfate.

3. The method according to claim 2, wherein said aqueous solution of homocystine sulfate is produced by heating methionine in the presence of sulfuric acid and a hydrogen halide.

4. The method of claim 1, wherein said base is an alkaline metal hydroxide.

5. The method according to claim 1, wherein said crude homocystine is produced by heating L-methionine in the presence of sulfuric acid and a hydrogen halide, contains mesohomocystine, and is obtained by neutralization using an alkaline metal hydroxide as the base so as to give a pH of 5 to 8 within 4 hours.

6. The method according to claim 1, wherein the molar ratio of the base to the crude homocystine is at least 2 to 1.

7. The method according to claim 1, wherein the temperature of base treatment is 50° C. or less.

8. A method of purifying homocystine comprising recovering homocystine by neutralizing an alkaline aqueous solution of crude homocystine containing polysulfide with an acid.

9. The method of claim 8, wherein the acid added is an organic acid.

10. A homocystine powder obtained from the method of claim 1 comprising polysulfide, wherein the homocystine powder contains no more than 1,000 ppm of polysulfide.

11. The homocystine powder according to claim 10, wherein the content of mesohomocystine is 1% by weight or less.

12. The method of claim 1, wherein the time of base treatment is 0.5 to 5 hours.

13. The method of claim 6, wherein the molar ratio of the base to the crude homocystine is from 3:1 to 10:1.

14. The method of claim 7, wherein the temperature of base treatment is 0 to 30° C.

15. The method of claim 8, wherein the acid is hydrochloric acid or sulfuric acid.

16. The method of claim 9, wherein the organic acid is selected from the group consisting of formic acid, acetic acid and oxalic acid.

17. The method of claim 8, wherein the recovering is filtration.

* * * * *